United States Patent [19]

Wheeler

[11] Patent Number: 5,208,280

[45] Date of Patent: May 4, 1993

[54] ELASTOMERS AND TIRE WITH N-ALKYL-P-QUINONEDIIMINO TRIAZINE STABILIZERS

[75] Inventor: Edward L. Wheeler, Watertown, Conn.

[73] Assignee: Uniroyal Chemical Company, Inc., Middlebury, Conn.

[21] Appl. No.: 890,496

[22] Filed: May 28, 1992

Related U.S. Application Data

[62] Division of Ser. No. 421,438, Oct. 13, 1989, Pat. No. 5,118,807.

[51] Int. Cl.$^5$ ............................................. C08K 5/34
[52] U.S. Cl. ..................................... 524/100; 544/197
[58] Field of Search ................................. 524/100

[56] References Cited

U.S. PATENT DOCUMENTS

| | | | |
|---|---|---|---|
| 2,909,421 | 10/1959 | Gysin et al. | 544/197 |
| 3,156,690 | 11/1964 | Dexter et al. | 544/197 |
| 3,202,681 | 8/1965 | Dexter et al. | 524/100 |
| 3,205,193 | 9/1965 | Dexter et al. | 524/100 |
| 3,255,191 | 6/1966 | Dexter et al. | 524/100 |
| 3,257,354 | 6/1966 | Dexter et al. | 524/297 |
| 3,379,676 | 4/1968 | Ashton et al. | 524/100 |
| 3,414,570 | 12/1968 | Coburn | 260/249.6 |
| 3,828,002 | 8/1974 | Westlinning et al. | 260/45.8 |
| 4,794,134 | 12/1988 | Wheeler et al. | 524/100 |
| 4,794,135 | 12/1988 | Wheeler et al. | 524/100 |

FOREIGN PATENT DOCUMENTS

| | | | |
|---|---|---|---|
| 0365127 | 4/1990 | European Pat. Off. | |
| 8105752 | 7/1982 | Netherlands | 524/100 |
| 922040 | 3/1963 | United Kingdom | 524/100 |

OTHER PUBLICATIONS

Chemical Abstracts vol. 65, 9116 (1966) I.C.I., "Heat Stabilized Polyamides". (ICI Ltd.).

Nakamura et al. Chemical Abstracts, vol. 102, entry 26067a (1985).

*Primary Examiner*—Paul R. Michl
*Assistant Examiner*—Olga Asinovsky
*Attorney, Agent, or Firm*—Raymond D. Thompson

[57] ABSTRACT

Novel N-alkyl-p-quinonediimino triazine compounds are disclosed which are useful as antiozonants for unsaturated high polymers. The compound may be prepared by oxidizing a 2,4,6-tris(N-alkyl-p-phenylenediamino) 1,3,5-triazine with a neutral or basic oxidizing agent and isolating the product.

2 Claims, No Drawings

ELASTOMERS AND TIRE WITH N-ALKYL-P-QUINONEDIIMINO TRIAZINE STABILIZERS

This is a divisional of application Ser. No. 07/421,438 filed Oct. 13, 1989, which has now issued on Jun. 6, 1992 as U.S. Pat. No. 5,118,807.

BACKGROUND OF THE INVENTION

This invention relates to new quinonediimine derivatives of triazine compounds which are useful as antiozonants for rubber, processes for their manufacture, and to their use in inhibiting the deteriorating effect of ozone on unsaturated polymers. In particular, novel N-alkyl-p-quinonediimino triazine compounds are described.

It is well known that ozone causes surface cracking of conventional highly unsaturated rubber vulcanizates when the rubber is placed under strain in an ozone environment. The most severe deterioration occurs when a small number of cracks are formed which grow rapidly into deep, disruptive fissures. These ozone cracks seriously shorten the serviceable life of the article.

The use of well known paraphenylenediamine materials has improved ozone protection under both static and dynamic conditions, however, even the best of the class have a very strong tendency to both stain and discolor. The term "stain" or "staining" is herein used to describe the characteristic of a material to diffuse through a polymeric substrate and discolor the adjacent surface. This diffusion staining is highly objectionable in most light colored rubber articles. In tires, which is the largest application in which the ozone protection is required, the tendency to diffusion staining of the aforementioned paraphenylenediamine materials is objectionable particularly in white sidewall type tires. Even in non-white sidewall type tires, the tendency of the materials to diffuse to the surface of the tire sidewall can be objectionable in that a brown or yellow dull surface is created on the tire sidewall. One common term for this phenomena is blooming. This is aesthetically objectionable in that it detracts from the general jet black, smooth appearance of a new tire. It is obvious that in a white sidewall tire, the migration of the brown or yellow discoloring material to the surface of the white sidewall is highly objectionable and generally difficult to remove during cleaning of the tire surface.

An object of this invention is to provide an antiozonant material which is highly effective in protecting the carcass from ozone attack. A further object is to provide ozone protection in a static condition at very low levels and to protect the rubber article during extended aging conditions against ozone attack. Yet another object is to produce a compound which does slowly diffuse and does not produce an objectionable brown or yellow bloom.

An advantage of the substituted triazine compounds is that it produces a substantially non-staining antiozonant of high molecular weight. A further advantage is that it slowly migrates to the surface of the rubber article. Another advantage is that the compounds do not tend to increase scorchiness of the compounded rubber stock in which it is used. This improves processing safety over other paraphenylenediamine antiozonants.

BRIEF DESCRIPTION OF THE INVENTION

The object and advantages of the invention may be obtained using the essential ingredient of the invention which is a compound of the general formula:

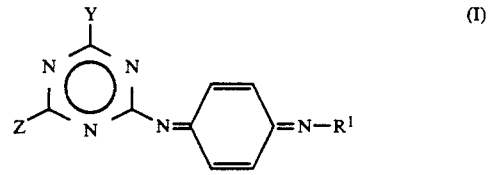

Y and Z are independently selected from

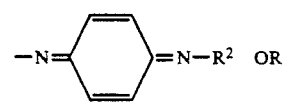

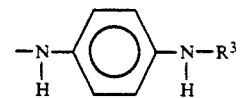

$R^1$, $R^2$ and $R^3$ are radicals independently selected from a $C_3$-$C_{18}$ branched or linear alkyl, or a $C_3$-$C_{12}$ cycloalkyl or a $C_3$-$C_{12}$ cycloalkyl substituted with one or more $C_1$-$C_{12}$ alkyl groups.

The products may be produced by a process of oxidizing a 2,4,6-tris(N-alkyl-p-phenylenediamino 1,3,5-triazine [sometimes referred to hereinafter as triazines or triazine intermediates] in the presence of an oxidizing agent. These triazines are known and taught in U.S. Pat. Nos. 4,794,135 and 4,794,134 which are incorporated herein by reference.

The novel compounds of the present invention may be prepared by a process comprising: reacting an N-alkyl-p-phenylenediamine with a tri-halo-triazine in a solvent to form a reaction mixture including a 2,4,6-tris(N-alkyl-p-phenylenediamino)-1,3,5-triazine trihydrohalide; and neutralizing said 2,4,6-tris(N-alkyl-p-phenylenediamino)-1,3,5-triazine trihydrohalide with a base to form a 2,4,6-tris(N-alkyl-p-phenylenediamino)-1,3,5-triazine;

Oxidizing said 2,4,6-tris(N-alkyl-p-phenylenediamino) 1,3,5-triazine in the presence of an oxidizing agent.

Unsaturated polymers may be stabilized against ozone degradation by incorporation therein of an effective amount of the novel compounds of structure (I).

DETAILED DESCRIPTION OF THE INVENTION

Refering now to structure (I), the preferred compositions are those in which $R^1$, $R^2$ and $R^3$ are linear or branched $C_3$-$C_{18}$ alkyl groups. The alkyl groups more preferred are those with a secondary carbon in the alpha position to the nitrogen. In this configuration, the antiozonant activity of the compound is believed to be enhanced. Therefore, the more preferred alkyl groups are branched chains which provide an alkyl substituent which is in accordance with this configuration. The cycloalkyl or $C_1$-$C_{12}$ alkyl substituted cycloalkyls provide such an alpha carbon configuration as well. The structure of formula I which is most preferred at this time are compounds in which $R^1$, $R^2$ and $R^3$ are $C_6$–$C_8$ branched chain alkyl groups. Examples of some preferred starting triazines of the present invention are: 2,4,6-tris(N-1,4-dimethylpentyl-p-phenylenediamino)-1,3,5-triazine; 2,4,6-tris(N-isopropyl-p-phenylenediamino)-1,3,5-triazine; 2,4,6-tris(N-cyclohexyl-p-phenylenediamino)-1,3,5-triazine; 2,4,6-tris(N-sec-butyl-p-phenylenediamino)-1,3,5-triazine; 2,4,6-tris(N-1,3-dimethylbutyl-p-phenylenediamino)-1,3,5-triazine; 2,4,6-tris (N-1- methylheptyl-p-phenylenediamino)-1,3,5- triazine; 2,4,6-tris(N-2,4-di-tert-butylcyclohexyl-p-phenylenediamino)-1,3,5-triazine; 2,4,6-tris(N-2-sec-butylcyclohexyl-p-phenylenediamino)-1,3,5-triazine; 2,4,6-tris(1-methyldecyl-p-phenylenediamino)-1,3,5-triazine. The most preferred material 2,4,6-tris(N-1,4-dimethylpentyl-p-phenylenediamino)-1,3,5-triazine.

The preferred compounds of this invention are the mono or bis or tris quinone diimines or mixtures of the foregoing materials. As shown in structure (I), the nomenclature for the mono, bis and tris materials is:

Mono quinonediimino triazine—
2,4-bis(N-1,4 alkyl-p-phenylenediamino)-6-(N-1,4-alkyl-p-quinonediimino)-1,3,5 triazine;

Bis quinonediimino triazine—
2-(N-1,4 alkyl-p-phenylenediamino)-4,6-bis (N-1,4-alkyl-p-quinonediimino)-1,3,5 triazine;

Tris quinonediimino triazine—
2,4,6-tris(N-1,4 alkyl-p-quinonediimino)-1,3,5-triazine.

The compounds of the invention can be synthesized advantagously by the following general method. Although the reagents may be added in different order as shown in some of the examples, the preferred method for preparation of the triazine intermediate is as follows:

The N-alkyl-p-phenylenediamine, which is prepared by methods known to those familiar with the art, is reacted with 2,4,6-tri-halogeno-1,3,5-triazine. A molar equivalent of the preferred tri-halo triazine commonly called cyanuric chloride is added as a powder to a solution of three plus moles of the N-alkyl-p-phenylenediamine in a suitable solvent such as isopropanol, at ambient temperatures with appropriate cooling. The first two halogen atoms are displaced rapidly. The reaction mixture is then heated to 60°–80° C. in order to complete the displacement of the third halogen atom. After 4–5 hours heating at 60°–80° C. the formation of the 2,4,6-tris-(N-alkyl-p-phenylenediamino)-1,3,5-triazine trihydrochloride is complete.

The process is unique in that the basicity of the alkyl-p-phenylenediamine allows the displaced halogen atom of the cyanuric halide to form the hydrohalide directly thereby enabling isolation of the trihalide and effecting a purification step.

The tris-hydrochloride may be removed by filtration, then reslurried in a suitable water miscible solvent, neutralized with aqueous base such as sodium hydroxide, and crystallized from the aqueous solvent mixture.

If the starting N-alkyl-p-phenylenediamine is sufficiently pure, or a less pure product is acceptable, isolation of the tris-hydrochloride is not necessary, and the reaction mixture can be neutralized and the product crystallized and isolated by filtration.

Temperature control of the reaction is of some importance. It is preferred that the first stage of the reaction take place below 30° C. and that the second stage take place at least 30° C. above the first stage. Selection of the optimal temperatures are, of course, dependent upon the identity of the p-phenylenediamine and solvent which is chosen.

Preferred solvents are alcohols although any suitable solvent may be utilized. The term solvent is meant to include an excess of the N-alkyl-p-phenylenediamine which may serve to solvate the reaction product and allow subsequent isolation.

The critical oxidation step may be carried out on the reaction mixture either after neutralization, after crystallization or after filtration. A preferred method is described below where the pure 2,4,6-tris(N-alkyl-p-phenylenediamino)1,3,5-triazine is redissolved and then oxidized. The oxidizing agent may be any known oxidant, which is neutral or basic in nature. In the process described below, the oxidizing agent is one which is preferentially soluble in an aqueous medium to simplify isolation of the final product.

The oxidation step preferably takes place in the presence of polar solvent(s) with an optional nonpolar co-solvent.

EXAMPLE 1

Preparation of a Mixture of Mono- and Bis-Quinonediimines derived from 2,4,6-tris(N-1,4 dimethylpentyl-p-phenylene-diamino)1,3,5-triazine The triazine (0.01 moles) was dissolved in a 1:1 mixture of acetonitrile and toluene. After adjusting the temperature to 25°–30° C., 0.02 moles of a 10–12% aqueous solution of sodium hypochlorite was added dropwise over 10–15 minutes. The mixture was stirred vigorously for two hours. The reaction mixture was quenched in water and the organic layer containing the product was separated. The solvent was removed by distillation under vacuum and the crude product mixture was recovered as a resinous solid. The assay of the material by high pressure liquid chromatography showed. 6% Tris, 60% Bis, 31% Mono and 3% starting triazine.

EXAMPLE 2

Preparation of a Mixture of Bis- and Tris-Quinonediimines derived from 2,4,6-tris(N-dimethylpentyl-p-phenylenediamino)-1,3,5-triazines The same procedure was used as above except that 3 equivalents of sodium hypochlorite were used per equivalent of the triazine. Work up of the product gave material having the following assay: 50% Tris, 43% Bis, 6% Mono, and less than 1% of the starting triazine.

Mono quinonediimino triazine—
2,4-bis(N-1,4 dimethylpentyl-p-phenylenediamino)-6-(N-1,4-dimethylpentyl-p-quinonediimino)-1,3,5 triazine.

Bis quinonediiminotriazine—
2-(N-1,4-dimethylpentyl-p-phenylenediamino)-4,6-bis(N-1,4-dimethylpentyl-p-quinonediimino)-1,3,5 triazine.

Tris quinonediimino triazine—
2,4,6-tris(N-1,4-dimethyl-pentyl-p-quinonediimino)-1,3,5-triazine.

The respective molecular weights by tandem mass spectroscopy were 692, 690; 688 respectively.

The general synthesis method follows the procedures above by substituting the appropriate 2,4,6-tris(N-alkyl-p-phenylene diamino)-1,3,5-triazine as the starting material. The oxizing agent may be changed to suit the physical form of the triazine starting material, solvents and cosolvents, reaction temperatures and desired isolation and purification procedures.

COMPARATIVE EXAMPLE A

Synthesis of Triazine Intermediates

EXAMPLE 1:
2,4,6-tris(N-1,4-dimethylpentyl-p-phenylene diamino)-1,3,5-triazine

In a 3-liter, four-necked, round-bottomed flask equipped with a thermometer, a mechanical stirrer, a condenser, and a dropping funnel was placed 1500 ml of isopropanol. The ispropanol was cooled to $-10°$ C. and 184.4 grams (1 mole) of cyanuric chloride was added. To this stirred suspension was added 680 grams (3.3 moles) of 4-amino-N-(1,4 dimethylpentyl)aniline dropwise over 1 hour period keeping the temperature between $-10°$ and $-5°$ C. Over 1 hour the reaction mixture was warmed to 30° C. then held for 16 hours at 30° C. The reaction mixture was refluxed for 1 hour at about 80° C. The reaction was followed by high pressure liquid chromatograph by observing the disappearance of the starting amine, and the conversion of the intermediate mono- and bis-substituted compounds to the final tris-substituted product. After cooling to 60° C. 240 grams (3 moles) of 50 percent sodium hydroxide solution was added dropwise over 1 hour period. The sodium chloride was removed by filtration at 40° C. The filtrate was cooled to 10° C. and the solvent was decanted off. The oily lower layer was extracted with water at 60° C. then crystallized from fresh isopropanol. The title compound was recrystallized from hexane and it melted at 128°-132° C. The yield was 78.1 percent. The infrared spectrum was consistent with the structure. Relative area HPLC analysis of the product showed it to be 95.8 percent pure.

The compounds of the invention are most advantageously utilized as antiozonants to protect blends of highly unsaturated polymers such as natural or synthetic elastomers. Representative of the highly unsaturated polymers which may be employed in the practice of this invention are diene elastomers. Such elastomers will typically possess an iodine number of between about 100 and about 250, although highly unsaturated rubbers having a higher or a lower (i.e., of 50-100) iodine number may also be employed. Illustrative of the diene elastomers which may be utilized are polymers based on conjugated dienes such as 1,3-butadiene; 2-methyl-1,3-butadiene; 1,3-pentadiene; 2 chloro-1,3 butadiene, 2,3-dimethyl-1, 3-butadiene; and the like, as well as copolymers of such conjugated dienes with monomers such as styrene, alpha-methylstyrene, acrylonitrile, methacrylonitrile, methyl acrylate, ethyl acrylate, methyl methacrylate, ethyl methacrylate, vinyl acetate and the like. Preferred highly unsaturated rubbers include natural rubber, cis-polyisoprene, polybutadiene, poly(styrene-butadiene), polychloroprene and poly(acrylonitrile-butadiene). Moreover, mixtures of two or more highly unsaturated rubbers may be employed. Also, mixtures of the highly unsaturated rubbers with elastomers having lesser unsaturation such as EPDM (ethylene-propylene-diene rubber), EPR (ethylene propylene rubber), butyl or halogenated butyl rubbers are most preferred in this invention.

The novel compounds of the invention may be used in combination with other antiozonants such as the triazines of U.S. Pat. No. 4,794,134 and less preferably with microcrystalline waxes as are commonly used to protect against static ozone attack. The other antiozonants which may be utilized include any of the commonly recognized paraphenylenediamine class of materials:

N-phenyl-N'-(1,3-dimethylbutyl)-p-phenylenediamine;
N-phenyl-N'-isopropyl-p-phenylenediamine;
N-phenyl-N'-(1-methylheptyl)-p-phenylenediamine;
N-phenyl-N'-cyclohexyl-p-phenylenediamine; mixed diaryl-p-phenylenediamines;
N,N'-diphenyl-p-phenylenediamine;
N,N'-di-beta-naphthyl-p-phenylenediamine;
N,N'-bis(1,4-dimethylpentyl)-p-phenylenediamine;
N,N'-bis(1-ethyl-3-methylpentyl)-p-phenylenediamine;
N,N'-bis(1-methylheptyl)-p-phenylenediamine;
N-phenyl-N'-p-toluenesulfonyl-p-phenylenediamine;
N-phenyl-N'-alkyl-p-phenylenediamine;
6-ethoxy-1,2-dihydro-2,2,4-trimethylquinoline; and nickel dibutyl dithiocarbamate.

The highly unsaturated polymers to be protected may be formulated in conventional manner with the many usual compounding ingredients, for example, vulcanizing agents, accelerators, activators, retarders, antiozonants, antioxidants, plasticizing oils and softeners, fillers, reinforcing pigments and carbon blacks.

The novel compounds of the invention may be added to an unsaturated polymer at a level of from 0.1 to about 10 parts by weight per hundred parts by weight of rubber hydrocarbon (hereinafter PHR). For these purposes the polymer is assumed to be a natural or synthetic rubber. A more preferred addition level is about 1 to about 8 parts PHR. The most preferred level is from about 2 to about 6 parts PHR. When the quinonediimino triazine compounds of the invention are used in combination with other antiozonants such as the paraphenylenediamine class of materials, they may be added in a blend which totals to the ranges set forth above. The compounds of the invention may be blended with the other antiozonants at ratios ranging from 1:3 to 3:1. More preferred is a ratio range of 2:3 to 3:2. These ratios are meant to indicate the percentages are 40:60 to 60:40 where in all cases the triazine compounds of the invention are the first number of each ratio. It should be noted that in certain applications and with certain other antiozonants, the PHR ranges of antiozonant listed above may be varied in order to obtain the optimal protection. Reasonable experimentation must be undertaken in order to optimize the ratios and overall levels of the blend when the triazine compounds of the invention are blended with other conventional antioxidants and antiozonants.

ANTIOZONANT UTILITY EXAMPLES 9-24

The quinone diimine derivatives of N-alkylarylenediamino triazine compounds of the invention function as outstanding antiozonants in rubber polymers with no migratory staining tendency evident at this time. The following examples demonstrate their utility in a variety of ozone and color stability test regimes. All tests utilize the triazines in vulcanized rubber compounds as are typical in the industry. The following test formulation is a typical rubber compound.

| TEST FORMULATION | |
| --- | --- |
|  | Parts by Weight |
| Natural Rubber (SMR5CV) | 50.0 |
| Polybutadiene (cis 1,4 BR) | 50.0 |
| Carbon Black (N-660) | 50.0 |

| TEST FORMULATION | |
|---|---|
| | Parts by Weight |
| Zinc Oxide | 3.0 |
| Stearic Acid | 1.0 |
| Aromatic Oil | 10.0 |
| Benzothiazole Sulfenamide | 1.0 |
| Sulfur (20% oil) | 2.0 |
| Antiozonant - Variable | 4.0 |

The foregoing test formulation was used for all test samples unless otherwise noted. The formulation is an approximation of a typical tire sidewall compound. The identity and level of the antiozonant are the variables to be evaluated in the subsequent examples.

The test formulation was utilized to make uncured test sheets by preblending the natural rubber and polybutadiene. Once blending was accomplished, all other ingredients except the sulfur and benzothiazole sulfenamide were added to form a nonproductive compound and in a subsequent mixing step, the foregoing ingredients were added. Tests sheets for the subsequent testing were cured in a platen press between heated plates for a time sufficient to achieve full cure. For the purposes of testing, a fifteen minute cure at 160° C. was normally utilized. The exact sample configuration of the test specimens for the ozone testing varies by the description of the ASTM method utilized. Reference is made to the ASTM test methods and such methods are incorporated herein by reference to abbreviate the required descriptive information regarding specimen preparation, test methods and test results.

OZONE TEST RESULTS

Ozone testing was conducted utilizing the standard test method of ASTM D1149-81 which is titled Rubber Deterioration - Surface Zone Cracking in a Chamber (Flat Specimen). This method covers the estimation of the resistance of vulcanized rubber to cracking when exposed to an atmosphere containing ozone. Rubber specimens are kept under a surface tensile strain and the ozone content in the test chamber is maintained at a 50 part per hundred million level (mPa) in a 100° F. (38° C.) test chamber. A common designation for this test is the bent loop test method since the test specimen is placed under strain by having it clamped in a looped configuration in which varying degrees of strain and elongation result. This bent loop configuration is an extremely severe test configuration in which failure can be expected in a relatively few hours given the high temperature and high ozone atmosphere in which the test samples are placed.

TABLE 1

| | Blank | Comparative A | Ex 1 | Ex 2 |
|---|---|---|---|---|
| Dynamic Ozone 96 Hrs @ 38° C. 50 (mPa) | Crack | Pass | Pass | Pass |
| Bloom Unaged | None | Yellow | Black | Black |
| Aged 3 days @ 100° C. | Brown | Black | None | NT |
| Outdoor Aging Lacquer | Fail | Pass | Pass | Pass |
| Staining Test* ASTM-D 925-83(C)* | + | 0 | + | + |

*Comparative A was used as the standard
+ is better than standard
NT = Not Tested Table 1 summarizes a series of antiozonant screening tests. The compounds of the invention (Examples 1 and 2) demonstrated excellent ozone protection, outdoor aging and staining characteristics. The tendency to bloom or discolor the surface of the rubber stock is improved over the yellow bloom of Comparative A. It should be noted that if a conventional paraphenylenediamine antiozonant [standard in tire industry] had been included in this series, it would have demonstrated a very high intensity brown bloom and severe staining characteristics in the lacquer test.

Industrial Applicability

The compounds of this invention are materials which are ideally suited for use as antiozonants in tire sidewalls, carcass and tread compositions. The excellent ozone resistance and non-staining characteristic is highly desirable in tire and rubber product. The fact that when blooming to the surface does occur it takes the form of a desirable flat black appearance which is invisible on the tire surface makes these materials more unique and desirable. This unique combination of characteristics sets these materials apart from all of the antiozonants of the prior art.

The quinone diimine derivatives of 2,4,6-tris(N-alkyl-p-phenylenediamino)-1,3,5-triazines can be most advantageously used in a tire as a component of any or all of the thermosetting rubber-containing portions of the tire. These include the tread, sidewall and carcass portions of a truck, passenger or off-road vehicle tire which also contain many different reinforcing layers therein. These components typically contain more than one thermosetting rubber polymer in a blend which must be protected from ozone degradation, as well as oxidative attack. Methods of incorporating these compounds into the tire are conventional and well known.

In view of the many changes and modifications that may be made without departing from principles underlying the invention, reference should be made to the appended claims for an understanding of the scope of the protection afforded the invention.

What is claimed is:

1. A degradation-resistant composition comprising:
   an unsaturated polymer having homogeneously incorporated therein an effective amount of one or more compounds of the general formula:

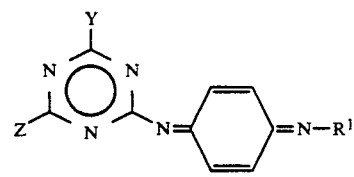

Y and Z are independently selected from

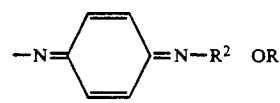 OR

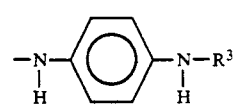

in which $R^1$, $R^2$ and $R^3$ are radicals independently selected from a $C_3$–$C_{18}$ branched or linear alkyl, or a $C_3$–$C_{12}$ cycloalkyl or a $C_3$–$C_{12}$ cycloalkyl substituted with one or more $C_1$–$C_{12}$ alkyl groups.

2. A tire having an elastomeric body including carcass, tread and sidewall portions, said elastomeric body comprising:

a plurality of thermosetting rubber polymers therein; and a plurality of reinforcing materials positioned within said body, at least one of said plurality of thermosetting rubber polymers having dispersed therein an antidegradant composition composed of one or more compounds of the general formula:

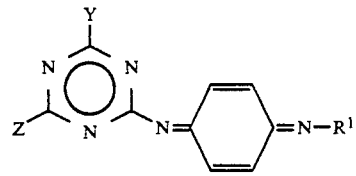

Y and Z are independently selected from

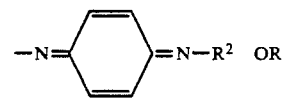

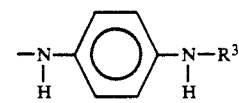

in which $R^1$, $R^2$ and $R^3$ are radicals independently selected from a $C_3$–$C_{18}$ branched or linear alkyl, or a $C_3$–$C_{12}$ cycloalkyl or a $C_3$–$C_{12}$ cycloalkyl substituted with one or more $C_1$–$C_{12}$ alkyl groups.

* * * * *